US008770020B2

(12) United States Patent
Oexman et al.

(10) Patent No.: US 8,770,020 B2
(45) Date of Patent: Jul. 8, 2014

(54) METHODS AND APPARATUSES FOR TESTING A SLEEP SUPPORT MEMBER

(75) Inventors: Robert D. Oexman, Carthage, MO (US); David B. Scott, Carthage, MO (US)

(73) Assignee: Kingsdown, Inc., Mebane, NC (US)

( * ) Notice: Subject to any disclaimer, the term of this patent is extended or adjusted under 35 U.S.C. 154(b) by 433 days.

(21) Appl. No.: 12/867,723

(22) PCT Filed: Feb. 13, 2009

(86) PCT No.: PCT/US2009/034020
§ 371 (c)(1),
(2), (4) Date: Aug. 13, 2010

(87) PCT Pub. No.: WO2009/102929
PCT Pub. Date: Aug. 20, 2009

(65) Prior Publication Data
US 2011/0004354 A1 Jan. 6, 2011

Related U.S. Application Data

(60) Provisional application No. 61/028,599, filed on Feb. 14, 2008.

(51) Int. Cl.
*A61B 5/103* (2006.01)
(52) U.S. Cl.
USPC ........................................... 73/172; 73/865.3
(58) Field of Classification Search
USPC ............................... 73/172, 774, 78–85, 865.3
See application file for complete search history.

(56) References Cited

U.S. PATENT DOCUMENTS

| 2,154,561 | A | * | 4/1939 | Breer et al. ..................... 73/819 |
| 2,395,787 | A | * | 2/1946 | Ledbetter et al. ................. 38/40 |
| 3,195,347 | A | * | 7/1965 | Janapol .......................... 73/806 |
| 3,334,517 | A | * | 8/1967 | Janapol .......................... 73/806 |
| 3,786,676 | A | | 1/1974 | Korolyshun et al. |
| 4,004,457 | A | * | 1/1977 | Eide et al. ....................... 73/818 |
| 4,140,008 | A | * | 2/1979 | Golembeck et al. ............. 73/78 |
| 4,183,224 | A | | 1/1980 | Rule, III et al. |
| 5,163,365 | A | * | 11/1992 | Taylor ............................ 100/38 |
| 5,231,717 | A | | 8/1993 | Scott et al. |
| 5,391,859 | A | * | 2/1995 | Hazan et al. ................... 219/250 |
| 5,641,917 | A | * | 6/1997 | Hurite et al. ................. 73/865.3 |
| 5,848,450 | A | | 12/1998 | Oexman et al. |
| 5,901,905 | A | | 5/1999 | Jung |
| 5,970,789 | A | * | 10/1999 | Meyer et al. ..................... 73/172 |

(Continued)

FOREIGN PATENT DOCUMENTS

| WO | 97/32509 A1 | 9/1997 |
| WO | 00/51470 A1 | 9/2000 |
| WO | 2007/053150 A1 | 5/2007 |

*Primary Examiner* — John Fitzgerald
(74) *Attorney, Agent, or Firm* — Sughrue Mion, PLLC

(57) ABSTRACT

Systems and methods for testing a sleep support member. A system including at least one pressing structure, wherein the at least one pressing structure includes at least one of a heater and a moisture device; and a controller configured to control pressing of the pressing structure onto the sleep support member, wherein the controller is configured to control at least one of heat provided by the heater and moisture provided by the moisture device. A method including controlling pressing of at least one pressing structure onto a sleep support member, wherein the at least one pressing structure includes at least one of a heater and a moisture device; and controlling at least one of heat provided by the heater and moisture provided by the moisture device.

30 Claims, 2 Drawing Sheets

(56) References Cited

U.S. PATENT DOCUMENTS

| | | |
|---|---|---|
| 6,220,088 B1 | 4/2001 | Scales et al. |
| 6,561,047 B1 * | 5/2003 | Gladney et al. ............ 73/865.3 |
| 6,571,192 B1 | 5/2003 | Hinshaw et al. |
| 6,585,328 B1 | 7/2003 | Oexman et al. |
| 6,741,950 B2 | 5/2004 | Hinshaw et al. |
| 6,792,819 B2 * | 9/2004 | Gladney et al. ............ 73/865.3 |
| 6,990,425 B2 | 1/2006 | Hinshaw et al. |
| 7,779,565 B2 * | 8/2010 | Jiang et al. .................. 38/103 |
| RE41,809 E | 10/2010 | Hinshaw et al. |
| 2003/0125899 A1 | 7/2003 | Hinshaw et al. |
| 2004/0003669 A1 * | 1/2004 | Gladney et al. ............ 73/865.3 |
| 2004/0215416 A1 | 10/2004 | Hinshaw et al. |
| 2009/0006027 A1 | 1/2009 | Hinshaw |
| 2009/0240514 A1 | 9/2009 | Oexman et al. |
| 2010/0317930 A1 | 12/2010 | Oexman et al. |
| 2010/0318239 A1 | 12/2010 | Oexman et al. |
| 2011/0010014 A1 | 1/2011 | Oexman et al. |

* cited by examiner

METHODS AND APPARATUSES FOR TESTING A SLEEP SUPPORT MEMBER

CROSS-REFERENCE TO RELATED PATENT APPLICATION

This application claims priority from U.S. Provisional Patent Application No. 61/028,599, filed on Feb. 14, 2008, in the U.S. Patent and Trademark Office, the disclosure of which is incorporated herein by reference in its entirety.

BACKGROUND

1. Technical Field

Methods and apparatuses consistent with the present invention generally relate to the testing of a sleep support member. More particularly, methods and apparatuses consistent with this invention relate to the testing of a mattress by simulating heat and/or moisture released by a person sleeping on the mattress and/or by simulating movement of the person sleeping on the mattress.

2. Description of the Related Art

There are several conventional tests for simulating the weight of a user sleeping on a mattress in order to determine the durability of the mattress. For example, the Cornell Testing Machine tests the durability of a mattress by repeatedly subjecting the mattress to a large force. Another example, the Mattress Rollator Machine, includes a weighted roller that simulates the weight and movement of a user by moving widthwise across the mattress. A mattress that has been subjected to these tests is evaluated based on how well it maintains its shape and support firmness.

In addition, U.S. Pat. No. 6,585,328 (the '328 patent), which is incorporated herein by reference in its entirety, and was invented by the same inventors as the present application, discloses a mattress evaluation system in which the deflection characteristics of the mattress are determined by simulating the weight of a sleeping person. That is, multiple pressure plates or platens are depressed downwardly into the mattress. The plates or platens are arranged so that the location of each plate or platen replicates a part of the person. Each platen is depressed by a pressure piston to simulate the weight of the person on the mattress. The suitability of the mattress for a person of a particular size is determined based on the sensed pressures.

However, each of these conventional systems has disadvantages because, although they simulate weight and movement on a mattress, they do not accurately simulate the movement of a human body on the mattress, the heat and/or moisture released from the human body, or the environmental conditions in which the mattress is used. For example, when the user of a mattress releases heat and perspires, the heat and perspiration can break down the fibers, foams and other soft materials on the top of the mattress. This can leave a permanent body impression or indentation in the mattress, which is a major problem especially with the plush materials employed in conventional mattresses.

Moreover, the mattress user typically changes his/her body position several times during the night, thus applying different pressures to different parts of the mattress. Conventional testing systems are not able to simulate this kind of motion and the resulting fatigue stress on the mattress.

Finally, the durability of a mattress changes based on the environmental conditions to which the mattress is exposed. Conventional testing systems are not able to simulate the environmental conditions in which the mattress is used.

SUMMARY

According to a first aspect of the present invention, there is provided system for testing a sleep support member, the system comprising: at least one pressing structure, wherein the at least one pressing structure includes at least one of a heater and a moisture device; and a controller configured to control pressing of the pressing structure onto the sleep support member, wherein the controller is configured to control at least one of heat provided by the heater and moisture provided by the moisture device.

A second aspect of the present invention provides a method for testing a sleep support member, the method comprising: controlling pressing of at least one pressing structure onto a sleep support member, wherein the at least one pressing structure includes at least one of a heater and a moisture device; and controlling at least one of heat provided by the heater and moisture provided by the moisture device.

A third aspect of the present invention provides a method for testing a sleep support member, the method comprising: providing a plurality of pressing structures, wherein each of the pressing structures includes at least one of a heater and a moisture device; controlling at least one of heat provided by the heaters and moisture provided by the moisture devices; and repeatedly pressing respective pressing structures onto the sleep support member for a period of time in accordance with a predetermined simulation pattern.

BRIEF DESCRIPTION OF THE DRAWINGS

The above and other aspects of the present invention will become more apparent by describing in detail illustrative embodiments thereof with reference to the attached drawings in which.

DETAILED DESCRIPTION OF ILLUSTRATIVE EMBODIMENTS OF THE INVENTION

Figure 1:
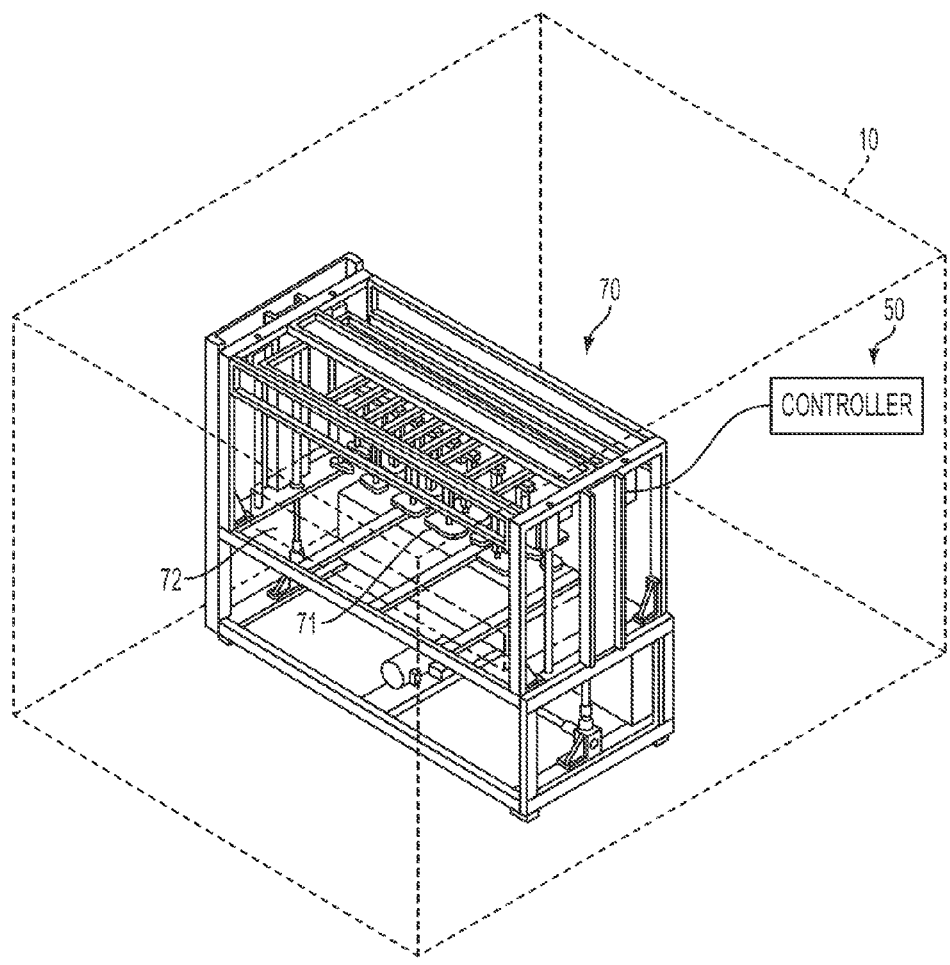
FIG. 1 shows a perspective view of a system for testing of a mattress according to an illustrative embodiment of the present invention.

Illustrative embodiments of the invention will now be described in detail with reference to the attached drawings in which like reference numerals refer to like elements.

Figure 2:
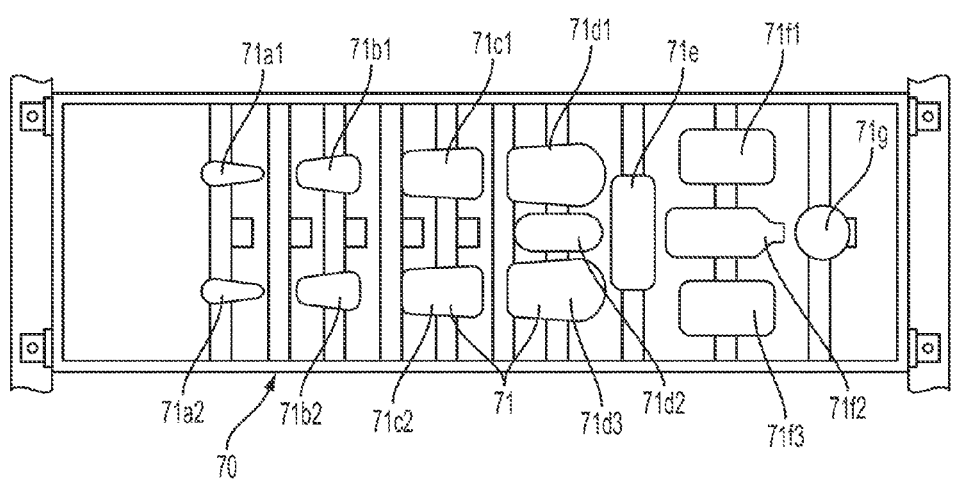
FIG. 2 shows a series of platens comprising a system for testing of a mattress according to an illustrative embodiment of the present invention.

FIGS. 1 and 2 show an illustrative embodiment of a system 70 for testing of a mattress consistent with the present invention. This illustrative embodiment uses pressing structures analogous to those of the mattress evaluation system of the '328 patent. The system 70 includes a series of plates or platens 71 that are arranged so that the location of each plate or platen 71 replicates a part of the human body, as shown in FIG. 2. For example, platen 71g replicates a person's head, while platens 71a1, 71a2 replicate the person's feet.

The platens 71 are repeatedly depressed downwardly into a mattress 72 that is being tested in a chamber 10 in accordance with a predetermined control pattern of a controller 50 that is used to simulate use of the mattress for an extended period of time (e.g., 15 years or the typical lifespan of a mattress).

However, the present invention is not limited to the pressing structures of the '328 patent. For example, a single pressing weight, one or more rollers, or an array of pressing platens could be used consistent with the present invention. The controller 50, can comprise, for example, a computer with a processor and a memory.

Figure 3:
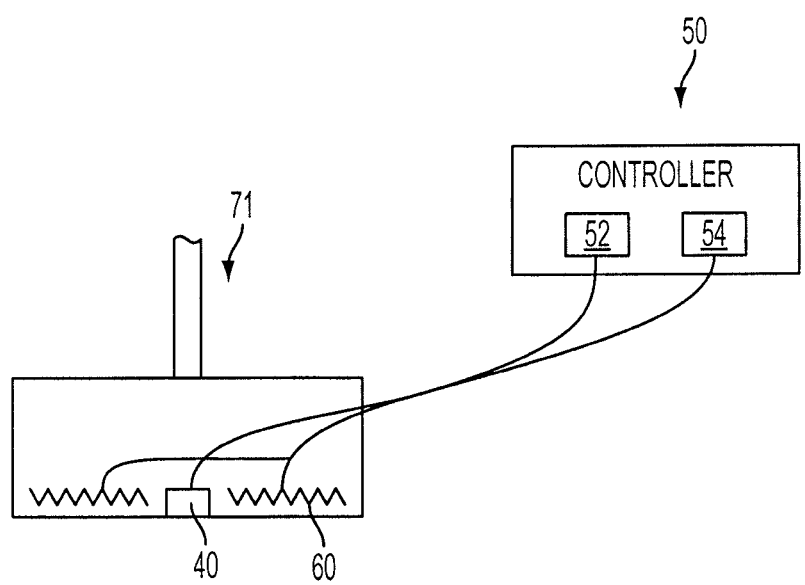
FIG. 3 shows a platen that is used with an illustrative embodiment, including heaters and moisture devices according to an illustrative embodiment of the present invention.

FIG. 3 shows a bottom surface of a platen 71 comprising a heater 60 and a moisture releasing device 40 that is used with the illustrative embodiment shown in FIGS. 1 and 2. Each of the platens 71 includes a heater 60 added at or near a bottom surface of the platen 71. The heating device 60 can be, for example, a resistive electrical heating element provided in a vicinity of a bottom of the platen 71, similar to what is used with a conventional clothing iron. The heating device 60 is controlled by a thermostat 52 so that the temperature of the platen 71 stimulates the temperature of a sleeping person. According to one illustrative embodiment, in order to properly change temperatures, the bottom of the platen 71 can be comprised of metal, for example, stainless steel or aluminum. However, the bottom of the platen is not limited to this configuration and can be comprised of a wide variety of suitable materials.

In addition, according to the illustrative embodiment shown in FIG. 3, a moisture releasing device 40, such as a nozzle or a valve, is added to the bottom of each platen 71. These moisture releasing devices 40 release a fluid, such as water or saline solution, onto the mattress 72 via the bottom of the platen 71. However, the present invention is not limited to the two aforementioned fluids and the moisture releasing devices 40 can release any fluid that simulates the effect of a human body on the mattress such as fluids that simulate perspiration or any other bodily fluid.

These moisture releasing devices 40 are controlled using a hygrometer 54 of the controller 50, which controls the amount of moisture released from the platens to simulate the amount of moisture released from a sleeping person. The fluid can be supplied to the platen 71 via or a hose or can be stored within the platen 71.

Accordingly, this illustrative embodiment can simulate, not only the weight of a person, but can also simulate the heat and the moisture released by a sleeping person. Thus, the effect of a sleeping person on the mattress can be more accurately simulated by adjusting the amount and frequency of application of the weight, heat, and moisture applied to the mattress based on value for an individual person for which the mattress is designed. The present invention is not limited to the heaters and moisture releasing devices of this illustrative embodiment and other structures can be used within the scope of the invention.

Moreover, the controller 50 can use a predetermined simulation pattern to control the individual movement and pressing of the pressing structures, e.g., platens 71, in order to simulate a person's movement on the mattress. For example, by providing a specific control of the individual pressing structures, the movement of a typical person throughout the night, e.g. movement from lying on his/her back to lying on his/her side, etc., can be more accurately simulated.

For example, referring to FIG. 2, in an illustrative method of the invention, the platens 71c1 and 71d1 are pressed first, simulating a person sitting on the side of the mattress, ready to go to sleep. Thereafter, a pressing force is applied by all of the platens 71 with the pressing force of each individual platen determined so as to simulate the force of a person sleeping on his/her back on the mattress.

Thereafter, throughout the simulation pattern the forces of the individual platens are adjusted to simulate a person rolling over on to his her side and/or to other positions. For example, a force can be applied to the platens 71a2, 71b2, 71c2, 71d2, 71d3, 71e, 71f2, 71f3, and 71g, while the other platens 71a1, 71b1, 71c1, 71d1 and 71f1 do not apply a force. This would simulate the person rolling to their side.

Assuming that the average person moves roughly 60 times a night, the forces of the individual platens 71 would change 60 times to various patterns, and then every 60 cycles, the person sitting on the side of the bed would again be simulated. Thus, the system 70 can literally simulate a person sitting on the edge of the bed as the person gets into bed at night, moving throughout the night, and then sitting on the edge of the bed again as the person gets up in the morning. The system 70 can even be used to simulate the forces that would be applied to the mattress over the mattress' lifetime, such as 15 years.

The invention is not limited to any specific pressing simulation pattern. The simulation pattern can be programmed based on the sleeping pattern of an individual person and controlled by the controller 50, and the movement of the platens 71 is repeated in order to simulate the forces applied during the lifetime of the mattress.

Moreover, a larger number of pressing elements 71 can be used to even more precisely simulate the movement of the person. The larger number of pressing structures also allows the system to simulate the forces applied by different sized people (i.e., persons of different heights, weights, weight distributions, etc.). For example, a six foot, six inch tall person would apply forces to the mattress at different positions and different magnitudes than a five foot tall person. As such, an array with, for example, ten or more columns and ten or more rows of pressing structures could provide a more precise system that could simulate the sleeping of different sized people. However, the present invention is not limited to the aforementioned embodiments and a smaller number of pressing elements may be employed consistent with the present invention. Alternatively, it is possible to instead change the positions of the pressing structures, such as by using motors and rails, in order to accommodate testing of different sized persons. Indeed, the present invention may be employed to simulate persons of any size, weight or body shape.

Thus, the controller 50 can control the necessary pressing elements so that a simulation for a particular person is provided when an operator of the controller 50 enters the weight and size characteristics of the person. Moreover, the heat and/or moisture characteristics of the particular person can be entered by the operator.

Alternatively, the tester can enter individual values for the characteristics (size, weight, heat, and moisture) based on percentiles. For example, all values of the fiftieth percentile would be entered if the average person were to be tested. Moreover, values of the $95^{th}$ percentile would be entered for heat and moisture, while values of the fiftieth percentile would be entered for weight and size, for an average sized person who happens to generate an extremely large amount of heat and sweat.

Although the sleeping environmental conditions throughout the United States are similar in many respects due to the use of indoor heating and air-conditioning systems, there are still variations in the environmental conditions in which the mattress is used. For example, the mattress conditions in a humid environment like Florida may still be different than those in Arizona. Therefore, the temperature and/or humidity of the testing environment in which the present invention is employed can be adjusted to simulate the environment in which the mattress will be used.

Moreover, in order to test a larger size mattress, such as a king or queen size, a larger system can be used or, alternatively, two systems can be used side by side to simulate the movement, heat, and moisture of two persons sleeping next to one another or can be used to calculate partner disturbance.

Although the illustrative embodiments discussed above uses pressing structures analogous to those of the mattress evaluation system of the '328 patent, the present invention is not limited to such a configuration. To the contrary, the concepts of the present invention can be applied to a wide variety of different pressing structures. For instance, the heaters and moisture releasing devices mentioned above could be a conventional Indention Load Deflection device, a Cornell machine, or more generally, any type of mattress testing device.

While the present invention has been particularly shown and described with reference to illustrative embodiments thereof, it will be understood by those of ordinary skill in the art that various changes in form and details may be made therein without departing from the spirit and scope of the invention as defined by the appended claims. For example, the controller of the illustrative embodiment is described as a single unit. However, the controller can instead be provided as multiple control units. The illustrative embodiments should be considered in a descriptive sense only and not for purposes of limitation. Therefore, the scope of the invention is defined not by the detailed description of the invention but by the claims set forth in the related non-provisional application and all differences within the scope will be construed as being included in the present invention.

What is claimed is:

1. A system for testing durability of a sleep support member, the system comprising:
   at least one pressing structure, wherein the at least one pressing structure includes at least one of a heater and a moisture device; and
   a controller configured to control pressing of the pressing structure onto the sleep support member,
   wherein the controller is configured to control at least one of heat provided by the heater and moisture provided by the moisture device that simulates at least one of heat and moisture expected to be released by a person sleeping on the sleep support member throughout a duration of at least one night, and
   wherein the controller is configured to control repeated pressing of the at least one pressing structure onto the sleep support member for a period of time in accordance with a predetermined simulation pattern.

2. The system of claim 1, wherein the controller is configured to control at least one of heat provided by the heater and moisture provided by the moisture device that simulates at least one of heat and moisture expected to be released by the person sleeping on the sleep support member throughout a duration of several nights.

3. The system of claim 1, wherein the controller is configured to control at least one of heat provided by the heater and moisture provided by the moisture device that simulates at least one of heat and moisture expected to be released by the person sleeping on the sleep support member throughout a duration of the sleep support member's expected lifetime.

4. The system for testing a sleep support member of claim 1, wherein the at least one pressing structure comprises a plurality of displaceable platens.

5. The system of claim 1, wherein the controller is configured to control testing durability of the sleep support member after the controlling pressing of the at least one pressing structure and the controlling the at least one of heat provided by the heater and moisture provided by the moisture device.

6. The system of claim 5, wherein the testing durability of the sleep support member comprises evaluating how well the sleep support member maintains shape and support firmness.

7. The system of claim 6, wherein the testing durability of the sleep support member comprises measuring a permanent indentation caused by the controlled pressing of the pressing structure onto the sleep support member.

8. The system for testing a sleep support member of claim 1, wherein the at least one of a heater and a moisture device comprises a heater and a moisture device, and
   wherein the controller is configured to control both heat provided by the heater and moisture provided by the moisture device that simulates both heat and moisture expected to be released by the person sleeping on the sleep support member throughout a duration of at least one night.

9. The system for testing a sleep support member of claim 8, wherein the heater comprises an electric heating element.

10. The system for testing a sleep support member of claim 8, wherein the moisture device comprises at least one of a valve and a nozzle.

11. The system for testing a sleep support member of claim 1, wherein the system further comprises a plurality of pressing structures,
    wherein each of the pressing structures includes at least one of a heater and a moisture device, and
    wherein the controller is configured to control at least one of heat provided by the heaters and moisture provided by the moisture devices.

12. The system for testing a sleep support member of claim 11, wherein the predetermined simulation pattern is configured to simulate a person's movement on the sleep support member.

13. The system for testing a sleep support member of claim 11, wherein the pressing structures are arranged so that a location of each respective pressing structure simulates a part of a human body.

14. The system for testing a sleep support member of claim 11, wherein positions of the pressing structures can be manually or automatically moved.

15. The system for testing a sleep support member of claim 11, wherein the controller controls at least one of heat and humidity of a chamber in which the sleep support member is provided that simulates at least one of heat and humidity of expected environmental conditions surrounding the sleep support member throughout a duration of at least one night.

16. The system for testing a sleep support member of claim 15, wherein the controller controls both heat and humidity of the chamber that simulates both heat and humidity of expected environmental conditions surrounding the sleep support member throughout a duration of at least one night.

17. The system for testing a sleep support member of claim 11, wherein the at least one of a heater and a moisture device comprises a heater and a moisture device.

18. The system for testing a sleep support member of claim 17, wherein the plurality of pressing structures comprises a plurality of displaceable platens.

19. The system for testing a sleep support member of claim 17, wherein the heater comprises an electric heating element and the moisture device comprises a valve or a nozzle.

20. A method for testing durability of a sleep support member, the method comprising:
    controlling pressing of at least one pressing structure onto a sleep support member,
    wherein the at least one pressing structure includes at least one of a heater and a moisture device;

controlling at least one of heat provided by the heater and moisture provided by the moisture device that simulates at least one of heat and moisture expected to be released by a person sleeping on the sleep support member throughout a duration of at least one night;

testing durability of the sleep support member after the controlling pressing of the at least one pressing structure and the controlling the at least one of heat provided by the heater and moisture provided by the moisture device; and controlling the repeated pressing of the at least one pressing structure onto the sleep support member for a period of time in accordance with a predetermined simulation pattern.

21. The method according to claim 20, wherein the predetermined simulation pattern simulates a person's movement on the sleep support member.

22. The method according to claim 20, further comprising controlling at least one of heat and humidity of a chamber in which the sleep support member is provided that simulates at least one of heat and humidity of expected environmental conditions surrounding the sleep support member throughout a duration of at least one night.

23. The method according to claim 22, further comprising controlling both heat and humidity of the chamber that simulates both heat and humidity of expected environmental conditions surrounding the sleep support member throughout a duration of at least one night.

24. A method for testing durability of a sleep support member, the method comprising:

providing a plurality of pressing structures, wherein each of the pressing structures includes at least one of a heater and a moisture device;

controlling at least one of heat provided by the heaters and moisture provided by the moisture devices that simulates at least one of heat and moisture expected to be released by a person sleeping on the sleep support member throughout a duration of at least one night;

repeatedly pressing respective pressing structures onto the sleep support member for a period of time in accordance with a predetermined simulation pattern; and testing durability of the sleep support member after the controlling the at least one of heat provided by the heaters and moisture provided by the moisture devices and the repeatedly pressing respective pressing structures onto the sleep support member.

25. The method according to claim 24, wherein the predetermined simulation pattern simulates a person's movement on the sleep support member.

26. The method according to claim 24, further comprising controlling the pressing structures so that a location of each respective pressing structure simulates a part of a human body.

27. The method according to claim 24, wherein positions of the pressing structures are automatically moved.

28. The method according to claim 24, wherein positions of the pressing structures are manually moved.

29. The method according to claim 24, further comprising controlling at least one of heat and humidity of a chamber in which the sleep support member is provided that simulates at least one of heat and humidity of expected environmental conditions surrounding the sleep support member throughout a duration of at least one night.

30. The method according to claim 24, further comprising controlling both heat and humidity of the chamber that simulates both heat and humidity of expected environmental conditions surrounding the sleep support member throughout a duration of at least one night.

* * * * *